United States Patent
Galimberti et al.

(10) Patent No.: US 10,737,997 B2
(45) Date of Patent: Aug. 11, 2020

(54) METHOD FOR THE MANUFACTURE OF FLUORINATED COMPOUNDS

(71) Applicant: SOLVAY SPECIALTY POLYMERS ITALY S.P.A., Bollate (IT)

(72) Inventors: Marco Galimberti, Bollate (IT); Vito Tortelli, Milan (IT); Emanuela Antenucci, Saronno (IT); Giuseppe Marchionni, Milan (IT)

(73) Assignee: SOLVAY SPECIALTY POLYMERS ITALY S.P.A., Bollate (MI) (IT)

( * ) Notice: Subject to any disclaimer, the term of this patent is extended or adjusted under 35 U.S.C. 154(b) by 0 days.

(21) Appl. No.: 16/089,903

(22) PCT Filed: Mar. 28, 2017

(86) PCT No.: PCT/EP2017/057238
§ 371 (c)(1),
(2) Date: Sep. 28, 2018

(87) PCT Pub. No.: WO2017/167705
PCT Pub. Date: Oct. 5, 2017

(65) Prior Publication Data
US 2019/0119192 A1    Apr. 25, 2019

(30) Foreign Application Priority Data
Mar. 31, 2016 (EP) .................... 16163104

(51) Int. Cl.
*C07C 51/41* (2006.01)
*C07C 68/00* (2020.01)

(52) U.S. Cl.
CPC .............. *C07C 51/41* (2013.01); *C07C 68/00* (2013.01)

(58) Field of Classification Search
None
See application file for complete search history.

(56) References Cited

U.S. PATENT DOCUMENTS

| | | |
|---|---|---|
| 3,271,341 A | 9/1966 | Garrison, Jr. |
| 3,900,372 A | 8/1975 | Childs et al. |
| 6,858,751 B1 | 2/2005 | Senet et al. |
| 7,053,237 B2 | 5/2006 | Okazoe et al. |

FOREIGN PATENT DOCUMENTS

| | | |
|---|---|---|
| EP | 1164122 A1 | 12/2001 |
| EP | 2058291 A1 | 5/2009 |
| GB | 1216639 A | 12/1970 |
| GB | 1226566 A | 3/1971 |
| JP | 2006321797 A | 11/2006 |
| WO | 2000059859 A1 | 10/2000 |
| WO | 2007140091 A1 | 12/2007 |
| WO | 2010003931 A1 | 1/2010 |
| WO | 2011003575 A1 | 1/2011 |

OTHER PUBLICATIONS

Flosser D.A. et al., "A useful conversion of alcohol to alkyl fluorides", Tetrahedron Lett., 2002, vol. 24, No. 23, pp. 4275-4279.
Olah G.A. et al., "Notes—Synthesis and investigation of Organic Fluorine Compounds. XXV. The preparation of Alkyl Fluoroformates and Remarks Relative to a New Published Preparation of Alkyl Fluorides", Journal of Organic Chemistry, 1956, vol. 21, No. 11, pp. 1319-1320.

*Primary Examiner* — Ana Z Muresan

(57) ABSTRACT

A method for the manufacture of perfluorinated compounds is herein disclosed. In particular, the method is useful for the manufacture of perfluorooxyalkyl carboxylic acid salts which can be used as surfactants. The method envisages the fluorination or a fluoroformate of an alcohol comprising a —$CH_2OCH_2$-moiety at a temperature equal to or higher than 20° C. and allows obtaining high yields and selectivity.

20 Claims, No Drawings

METHOD FOR THE MANUFACTURE OF FLUORINATED COMPOUNDS

CROSS-REFERENCE TO PREVIOUS APPLICATIONS

This application is a U.S. national stage entry under 35 U.S.C. § 371 of International Application No. PCT/EP2017/057238 filed Mar. 28, 2017, which claims priority to European patent application No. EP 16163104.9, filed Mar. 31, 2016. The entire contents of these applications are explicitly incorporated herein by this reference.

TECHNICAL FIELD

The present invention relates to a method for the manufacture of fluorinated compounds, in particular for the manufacture of perfluorooxyalkyl carboxylic acid derivatives which can be used as surfactants.

BACKGROUND ART

Fluorinated surfactants have been long since used in emulsion polymerization process for the manufacture of fluoropolymers.

Traditionally, perfluorocarboxylic acid derivatives have been employed in said processes; however, due to environmental concerns related to the use of such compounds, fluorosurfactants comprising an oxygen-containing side chain have attracted increasing attention as emulsifiers. In particular, perfluorooxycarboxylates of general formula: $R_fO-CF_2CF_2-O-CF_2-COOX$, wherein $R_f$ is a perfluoro(oxy)radical and X is an alkali metal cation or an ammonium cation have been considered.

Such perfluorooxycarboxylates were first disclosed in U.S. Pat. No. 3,271,341 (E.I. DU PONT DE NEMOURS) Sep. 6, 1966. This document teaches a manufacturing method wherein tetrafluoroethylene epoxide is polymerized in the presence of a suitable free-radical forming compound (e.g. activated charcoal) at low temperature, resulting in polyethers having general formula: $CF_3CF_2-O-(CF_2CF_2-O)_n-CF_2COF$, with n being an integer from 0 to 10. Subsequent distillation affords various fractions differing from one another in their polymerization degree: corresponding acids or salts are obtained from the acyl fluoride derivatives by hydrolysis and, for salts, simultaneous or subsequent reaction with a base. Nevertheless, this process suffers from the disadvantage that a distribution of polyether surfactants is obtained, so that yields of single particular target compounds might be low and the separation Steps for isolating the same very burdensome.

Since then, a number of alternative methods for the manufacture of perfluorooxycarboxylates have been developed, for example those disclosed in EP 1164122 A (ASAHI GLASS CO LTD) Dec. 19, 2001, U.S. Pat. No. 7,053,237 (ASAHI GLASS CO LTD) Nov. 24, 2005, JP 2006321797 (ASAHI GLASS CO LTD) Nov. 30, 2006, EP 2058291 A (ASAHI GLASS CO LTD) May 13, 2009, WO 2007/140091 (3M INNOVATIVE PROPERTIES COMPANY) Dec. 6, 2007, WO 2010/003931 A (SOLVAY SOLEXIS S.P.A.) Jan. 14, 2010 and WO 2011/003575 (SOLVAY SOLEXIS S.P.A.) Jan. 13, 2011

Some of such methods involve the fluorination of alcohols comprising at least one C—H bond and an ethereal oxygen atom; however, hydrocarbons containing functional hydroxyl moieties are generally unstable under conditions of traditional fluorination processes. Under such conditions, it is generally understood that compounds having hydroxyl groups decompose, with simultaneous release of HF and $COF_2$, and subsequent formation of corresponding non-functional perfluorocompounds having one less carbon atom than the starting hydroxyl-containing compound. Therefore, such alcohols must be protected before fluorination, for example by conversion into esters of perfluorinated carboxylic acids or as esters of fluoroformic acid. Decomposition problems can be even more serious when the starting alcohol comprises a moiety of formula $-CH_2OCH_2-$, which is easily cleaved in the presence of HF developed in the course of the reaction.

In particular, EP 1164122 A discloses a process for producing fluorinated compounds wherein a primary hydrogenated alcohol is first converted into the corresponding ester, generally a partially fluorinated ester, as obtained by reaction with a (per)fluorinated acyl fluoride, and then subjected to fluorination in liquid phase. The so-obtained perfluorinated ester can be then thermally cleaved or decomposed with suitable agents, to obtain perfluorinated acyl fluoride corresponding to the starting hydrogenated alcohol.

Similarly, U.S. Pat. No. 7,053,237 discloses a process for producing a fluorinated ester, wherein a primary hydrogenated alcohol is protected via transesterification and then subjected to fluorination in liquid phase.

However, the above described processes have the drawback that, in order to prevent decomposition of the reagents due to the reaction exothermicity, it may be necessary to operate under diluted concentrations both of fluorine and of the hydrogen-containing alcohol. Furthermore, to obtain a fully fluorinated product, a large excess of fluorine over the stoichiometrically required quantity, is needed. These conditions might negatively affect the reaction rate, yielding low productivity of the overall process.

Furthermore, as already mentioned, in order to reduce fluorine consumption, protection of the alcohol moiety as an ester is generally performed using suitable perfluorinated carboxylic acid derivatives, generally acyl fluorides, whose availability might be costly and induce further Steps for appropriate separation, recovery and reuse.

As an alternative, hydrogen-containing alcohols can be protected under the form of fluoroformates before being submitted to fluorination.

Thus, U.S. Pat. No. 3,900,372 (PHILLIPS PETROLEUM) Aug. 19, 1975 discloses a process for the production of perfluorinated organic compounds from hydrogen-containing alcohols. The process comprises protection of the hydroxyl moieties of the hydrogen-containing alcohol by reaction with carbonyl fluoride to yield corresponding hydrogen-containing fluoroformates. Said fluoroformates are then subjected to an electrochemical fluorination Step, and the resulting perfluorinated counterparts still possessing the fluoroformate functionality are subsequently cleaved by the action of fluoride ions under reacting conditions for yielding corresponding acyl fluorides. Further, it is known that perfluorinated fluoroformates can be converted into fluoroacyl fluorides with loss of carbonyl fluoride, easy to separate and recover.

However, electrochemical fluorination is a burdensome and energy-consuming procedure, which is generally less economically and industrially acceptable than fluorination with elemental fluorine. Furthermore, yields in electrochemical fluorination are known to be mostly moderate or even poor, especially if high molecular weight compounds have to be fluorinated.

Attempts to fluorinate with molecular fluorine certain fluoroformates were disclosed in GB 1226566 (MONTE- CATINI EDISON) Mar. 31, 1971; this document teaches a process for the preparation of certain perfluorinated polyethers wherein possible terminal groups of acidic nature, such as formate moiety, are eliminated. Conversion by severe heat treatment of a perfluorinated polyether having a fluoroformate terminal group into a fluoroacyl fluoride is also described.

According to WO 2011/003575, fluorinated compounds, in particular perfluorooxycarboxylates, can be obtained by:

A. converting an at least partially hydrogenated alcohol into corresponding at least partially hydrogenated fluoroformate compound;

B. reacting said at least partially hydrogenated fluoroformate compound with fluorine in the presence of at least one (per)haloolefin comprising at least one carbon-carbon double bond and having at least one fluorine or chlorine atom on either one of the carbon atoms of said double bond, to obtain a perfluorinated fluoroformate compound; and C. cleaving and hydrolysing the perfluorinated fluoroformate compound.

This method allows carrying out the fluorination Step under mild conditions, thereby achieving high yields and selectivity and complete fluorination of the starting alcohol without using large amounts of fluorine. In particular, this document teaches that, in the fluorination reaction, the reagents can be used even without solvents and that the temperature can be maintained in the range of −100 to +50° C., without observing decomposition of the reagents; in the examples, an acyl fluoride of a partially fluorinated cyclic ether which does not comprise a —$CH_2OCH_2$— moiety is submitted to fluorination at a temperature of at most 5° C. However, the Applicant has observed that, even in the presence of a (per)haloolefin, alcohols comprising —$CH_2OCH_2$— are still susceptible to degradation when the fluorination reaction is carried out at a lower temperature than 0° C.

SUMMARY OF INVENTION

The Applicant has now found out that fluoroformates of alcohols comprising at least one —$CH_2OCH_2$— moiety can be submitted to fluorination with fluorine at temperatures equal to or higher than 20° C., even in the absence of a (per)haloolefin, without undergoing significant degradation and with yields of fluorinated product considerably higher than those obtained when the reaction is carried out at lower temperatures, in particular at temperatures below 0° C. This finding is surprising is view of the fact that it would be expected that, the lower the temperature, the lower the risk of degradation of the sensitive reagents.

For the avoidance of doubt, as intended herein, the term "fluoroformate" denotes any compound which can be represented with formula R—O—C(O)—F and which can be regarded as the product of an esterification reaction of an alcohol R—OH with fluoroformic acid (FCOOH).

Accordingly, the present invention relates to a method for the manufacture of fluorinated compounds which comprises:

a) providing a fluoroformate [fluoroformate (I)] of an alcohol [alcohol (II)] comprising at least one —$CH_2OCH_2$— moiety;

b) submitting the fluoroformate (I) to fluorination with elemental fluorine, optionally in the presence of a (per)haloolefin, at a temperature of at least 20° C., to obtain the corresponding perfluorinated fluoroformate [fluoroformate (III)] and, optionally, c) cleaving the perfluorinated fluoroformate (III).

According to one embodiment of the invention, the fluoroformate (I) complies with formula (I-A)

$$R^1CH_2—O—C(O)—F \qquad (I\text{-}A)$$

and is obtained from an alcohol (II) complying with formula (II-A):

$$R^1CH_2OH \qquad (II\text{-}A)$$

wherein $R^1$ is an optionally fluorinated straight or branched alkyl group comprising at least one ethereal oxygen atom comprised in a —$CH_2OCH_2$— moiety and, optionally, at least one further ethereal oxygen atoms and/or cycloalkylene moieties.

Preferably, a cycloalkylene moiety is a $C_5$-$C_6$ cycloalkylene, optionally bearing one or more straight or branched $C_1$-$C_4$ alkyl groups.

Preferably, the fluoroformate (I) complies with formula (I-B)

$$R^2—CH_2OCH_2(CH_2)_n O—C(O)—F \qquad (I\text{-}B)$$

and is obtained from an alcohol (II) complying with formula (II-B):

$$R^2—CH_2OCH_2(CH_2)_n OH \qquad (II\text{-}B)$$

wherein:

$R^2$ is an optionally fluorinated straight or branched alkyl group, optionally comprising at least one ethereal oxygen atom and/or cycloalkylene moiety and n is an integer ranging from 1 to 10, preferably from 1 to 4. More preferably, n is 1.

For the avoidance of doubt, in the following description, when ranges are indicated, range ends are included.

Preferably, in formula (II-B), n is 1 and $R^2$ is an optionally fluorinated straight or branched alkyl group comprising from 1 to 20 carbon atoms and, optionally, one or more ethereal oxygen atoms.

More preferably, in formula (II-B), n is 1 and $R^2$ is a straight alkyl group comprising from 1 to 20 carbon atoms and at least one ethereal oxygen atoms.

For the avoidance of doubt, the at least one ethereal oxygen atom comprised in group $R^2$ can either interrupt the alkyl group or bridge said group to the —$CH_2OCH_2(CH_2)_n OH$ group.

Preferred examples of alcohols (II) are those complying with formulae:

$CH_3OCH_2CH_2OH$ (ethyleneglycol monomethyl ether)
$CH_3CH_2OCH_2CH_2OH$ (ethyleneglycol monoethyl ether)
$CH_3CH_2CH_2OCH_2CH_2OH$ (ethyleneglycol monopropyl ether)
$CH_3CH_2CH_2CH_2CH_2OCH_2CH_2OH$ (ethyleneglycol monobuthyl ether)
$CH_3OCH_2CH_2OCH_2CH_2OH$ (diethyleneglycol monomethyl ether)
$CH_3CH_2OCH_2CH_2OCH_2CH_2OH$ (diethyleneglycol monoethyl ether)
$CH_3CH_2CH_2OCH_2CH_2OCH_2CH_2OH$ (diethyleneglycol monopropyl ether)
$CH_3CH_2CH_2CH_2OCH_2CH_2OCH_2CH_2OH$ (diethyleneglycol monobuyl ether)
$CH_3OCH_2CH_2CH_2OCH_2CH_2OH$ (ethyleneglycol monomethoxypropyl ether)

CH$_3$OCH$_2$CH$_2$OCH$_2$CH$_2$OCH$_2$CH$_2$OH (triethyleneglycol monomethyl ether)

CH$_3$CH$_2$OCH$_2$CH$_2$OCH$_2$CH$_2$OCH$_2$CH$_2$OH triethyleneglycol monoethyl ether)

CH$_3$CH$_2$CH$_2$OCH$_2$CH$_2$OCH$_2$CH$_2$OCH$_2$CH$_2$OH (triethyleneglycol monopropyl ether)

CH$_3$CH$_2$CH$_2$CH$_2$OCH$_2$CH$_2$OCH$_2$CH$_2$OCH$_2$CH$_2$OH (triethyleneglycol monobuyl ether).

The alcohol of formula CH$_3$CH$_2$OCH$_2$CH$_2$OCH$_2$CH$_2$OH (diethylenglycol monoethyl ether) is particularly preferred, as it allows obtaining fluorosurfactants of formula CF$_3$CF$_2$OCF$_2$CF$_2$OCF$_2$COOM, wherein M is an alkali metal or an ammonium ion, which are particularly useful in fluoromonomer emulsion polymerization.

Alcohols (II) can be obtained according to methods known in the art.

Step a) is typically carried out by submitting an alcohol (II) with a reagent selected from the group consisting of carbonyl fluoride, carbonyl fluoride bromide and carbonyl fluoride chloride according to known methods. Preferably the reagent is carbonyl fluoride.

Standard methods for converting an alcohol into a fluoroformate can be used. Among others, suitable methods are notably described in GB 1216639 (BAYER AG) Dec. 23, 1970, WO 00/59859 (ISOCHEM SA) Oct. 12, 2000, FLOSSER, D. A., et al. A useful conversion of alcohol to alkyl fluorides. *Tetrahedron lett.* 2002, vol. 24, no. 23, p. 4275-4279, OLAH, G. A., et al. Notes—Synthesys and investigation of Organic Fluorine Compounds. XVV. The preparation of Alkyl Fluoroformates and Remarks Relative to a New Published Preparation of Alkyl Fluorides. *Journal of Organic Chemistry.* 1956, vol. 21, no. 11, p. 1319-1320.

According to one embodiment, the reaction between alcohol (II) and the above-mentioned reagent can be represented as follows:

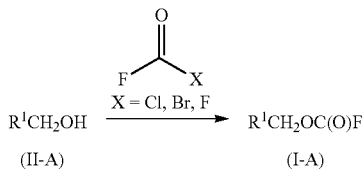

wherein R$^1$ is as defined above.

In case carbonyl fluoride is used, this reagent may be obtained by feeding fluorine, optionally mixed with an inert gas, and carbon monoxide to a reactor in the gas phase and continuously feeding the so obtained carbonyl fluoride to a further reaction vessel containing said alcohol (II). In this case, the molar ratio of carbon monoxide to fluorine (CO/F$_2$) is preferably not less than 1.0, to allow fluorine to fully react with carbon monoxide.

In Step a), alcohol (II) can be used pure, provided that it is liquid in the reaction conditions, or it can be diluted or dissolved in a suitable solvent. Among suitable solvents, mention can be notably made of organic halogenated compounds, such as methylene chloride, organic nitriles, such as acetonitrile, perchlorofluoroethers, such as CF$_3$OCFClCF$_2$Cl, perfluoropolyethers or hydrogen-containing fluoropolyethers (e.g. those commercialized under trade name GALDEN® PFPE or H-GALDEN® PFPE by Solvay Specialty Polymers Italy S.p.A.), fluorinated or perfluorinated ethers (e.g. those commercialized under trade name NOVEC® fluids and HFE® ethers from 3M).

When alcohol (II) is completely converted into fluoroformate (I), any residual carbonyl fluoride, carbonyl fluoride bromide or carbonyl fluoride chloride is vented away by means of an inert gas and any optional solvent is removed according to conventional methods, typically by distillation. Thereafter, the fluoroformate (I) can be directly submitted to Step b) without further purification.

According to one embodiment, the fluorination reaction of fluoroformate (I) with fluorine can be represented as follows:

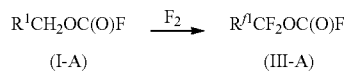

wherein R$^{f1}$ is the perfluorinated equivalent of R$^1$.

For the avoidance of doubt, as intended herein, the expression "fluorination reaction" does not comprise electrochemical fluorination.

Step b) is carried out by contacting the fluoroformate (I) with fluorine at a temperature equal to or higher than 20° C. Fluorine can be used either pure or diluted in an inert gas, such as nitrogen, argon or helium. Typically, fluorine is diluted in an inert gas. The reaction temperature can be as high as the lowest between the boiling temperature of the fluoroformate (I), of the solvent, if used, or of any azeotropic mixture between the fluoroformate (I) and solvent. However, it is preferred that the temperature is kept in a range between 20° C. and 100° C., more preferably between 20° C. and 50° C.

Even though under these conditions conversion rates of fluoroformate (I) into fluoroformate (III) are high and the contact time of the fluoroformate (I) with HF developed in the course of the reaction is reduced, a HF scavenger (e.g. NaF, KF) can optionally be used.

Step b) can be carried out semicontinuously or continuously, in one or more solvents or, if the fluoroformate (I) is liquid under the reaction conditions and if the reaction exothermicity does not require a solvent to dilute or dissolve the reactants, in a non-solvent phase. When a solvent is used, the person skilled in the art will be able to select it among one or more of those resistant to fluorine attack under the reaction conditions; typically, the solvent is selected from chlorofluorocarbon (CFCs), perfluoro(poly)ethers, chlorofluoroethers, and tertiary perfluorinated amines. In one preferred embodiment, the solvent is a CFC; a convenient example of CFC is 1,2,3,4-tetrachloro hexafluorobutane.

According to one embodiment, Step b) is carried out semicontinuously and in the presence of one or more solvents. In such embodiment, the selected one or more solvent is placed in the reaction vessel and fluorine is fed until saturation of the solvent(s); thereafter, the fluoroformate (I) is also fed in the reaction vessel, keeping at temperature of at least 20° C. Preferably, the fluroroformate (I) is fed and, simultaneously and independently, feeding of fluorine is continued. In other words, the fluoroformate (I) is fed in the reactor through an inlet tube, while fluorine is fed simultaneously through another inlet tube. When the feeding of both reagents is terminated, the resulting crude product, comprising the fluoroformate (III) is submitted to $^1$H- and/or $^{19}$F- NMR analysis and, if fluorination is not complete, further treatment with one or more (per)halolefins, preferably one (per)haloolefin, can be carried out as disclosed in WO 2011/ 003575, herein incorporated by reference. The amount of (per)haloolefin is not critical; however, it is typically comprised in the range of 0.1% to 50% moles, preferably in the range of 0.5% to 30% moles with respect to the molar amount of fluorine fed in the reactor to complete fluorination.

According to another embodiment, Step b) is carried out continuously. In this embodiment, fluorine, the fluoroformate (I) and, optionally, one or more solvents are fed in a reactor at a certain flow rate until reaching the steady state. As intended herein, the term "steady state" means that the concentration of the reagents and reaction products in the reactor is the same as the concentration of the unreacted reagents and reaction products flowing out the reactor. For the avoidance of doubt, the expression "reaction product" is intended to include the perfluorinated fluoroformate (I) and any possibly formed by-products.

A (per)haloolefin can optionally be used also when Step b) is carried out continuously in order to further promote complete fluorination, reduce reaction times and further optimize the yields. In such case, the (per)haloolefin is fed in the reactor with fluorine, the fluoroformate (I) and any optional solvent.

The (per)haloolefin can be added at any time of Step b). Thus, for the avoidance of doubt the expression "optionally in the presence of a (per)haloolefin" means that the (per) haloolefin can be added at any time of Step b). However, when the process is carried out continuously, it is preferred to feed the (per)haloolefin since the beginning.

The term "(per)haloolefin" denotes a fully or partially halogenated olefin comprising at least one carbon-carbon double bond and having at least one fluorine or chlorine atom on either one of the carbon atoms of said double bond.

Suitable (per)halolefins of that sort are those disclosed in WO 2011/003575. Advantageously, the (per)haloolefin is a perhaloolefin selected from tetrafluoroethylene (TFE), hexafluoropropylene (HFP) and its dimers and trimers, octafluorobutene, perfluoropentene, perfluorohexene, perfluoroheptene and perfluorooctene. More advantageously, the perhaloolefin is selected from tetrafluoroethylene (TFE), hexafluoropropylene (HFP) and its dimers and trimers. In a preferred embodiment, the perhaloolefin is hexafluoropropylene (HFP).

The crude fluoroformate (III) obtained from Step b) can be directly submitted to Step c).

Any suitable cleaving or decomposition method or reaction may be used in Step c). A cleaving reaction may be accomplished by thermolysis in the presence of metal fluorides, such as NaF, CaF$_2$, BaF$_2$, AgF, CsF, KF. The temperature for the thermolysis reaction may be comprised in the range of –70° C. to 220° C.; preferably, the temperature may be comprised in the range of –30° C. to 150° C. This reaction leads of an acyl fluoride [acyl fluoride (IV)] which can be further submitted to hydrolysis and neutralization with a hydroxide. In one exemplary embodiment, the decomposition reaction can be represented as follows:

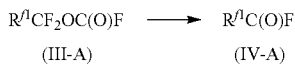

(III-A)      (IV-A)

wherein R$^{f1}$ is as defined above.

Advantageously, Step c) is carried out by directly submitting the crude fluoroformate (III) to treatment with a hydroxide. Typically, the crude product from Step b) is contacted with an aqueous solution of a hydroxide of formula (f-1):

$$M^+OH^-$$ (f-1)

wherein M represents a monovalent metal or an ammonium group.

As intended herein, a monovalent metal is a metal selected from those of group (I) of the periodic table; preferably, the metal is sodium or potassium. In a preferred embodiment, the metal is potassium.

As intended herein, an ammonium group is one of formula NR$^N_4$, wherein R$^N$, equal to or different at each occurrence, is hydrogen or a C$_1$-C$_6$ hydrocarbon group.

In one embodiment, the direct treatment of a fluoroformate (III) with a hydroxide can be represented as follows:

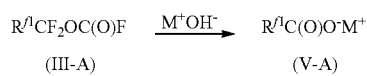

(III-A)      (V-A)

wherein R$^{f1}$ and M are as defined above.

The molar amount of hydroxide of formula (f-1) is at least six times the molar amount of fluoroformate (III). The reaction is monitored by taking samples and by submitting the aqueous layer to $^{19}$F-NMR; when the analysis reveals complete conversion of the —C(O)F groups into —C(O) OM groups, the aqueous layer is separated to recover the desired carboxylate salt.

Carrying out Step c) by direct treatment with a hydroxide is particularly convenient when the fluorinated compound of interest is a carboxylate salt [salt (V)].

The method of the invention can be carried out using conventional equipment suitable for carrying out fluorination reactions. However, in a preferred embodiment, Step b) is conveniently carried out in a microreactor, preferably a falling film microreactor (FFMR), according to methods known in the art. Within the present description, the term "microreactor" (otherwise referred to as "microstructured reactor" or "microchannel reactor") is intended to mean a device in which chemical reactions take place in a confinement with typical cross-sectional dimensions below 1 mm. Said confinements are typically microchannels (also referred to as fine "flow ducts"), which are channels with a cross sectional dimension below 1 mm.

Carrying out Step b) in a microreactor has the advantages of further reducing the contact times between the species involved; thus, the risk that any HF developed in the course of the reaction degrades the starting alcohol is even lower. A further advantage of carrying out Step b) in a microreactor is that the use of solvents can be avoided even in cases wherein the reaction exothermicity is high.

The invention will be disclosed in greater detail in the following experimental section by means of non-limiting examples.

Should the disclosure of any patents, patent applications, and publications which are incorporated herein by reference conflict with the description of the present application to the extent that it may render a term unclear, the present description shall take precedence.

EXPERIMENTAL SECTION

Materials and Methods

Commercially available diethylenglycol monoethyl ether (CH$_3$CH$_2$OCH$_2$CH$_2$OCH$_2$CH$_2$OH), 1,2,3,4-tetrachloro hexafluorobutane, hexafluoropropene (CF$_3$CF=CF$_2$), KOH and any other chemicals were used as received by the manufacturer.

A Falling Film Microreactor (FFMR) supplied by Fraunhofer Institute for Chemical Technology ITC, Branch IC- IMM (Institut für Mikrotechnik Mainz GmbH) was used, having a surface to volume ratio of about 20000 m²/m³ and comprising five U-shaped trenches (each having a volume of about 80 microliters) and a sealed gas chamber located on the top of the trenches. The microreactor was exercised in co-current, i.e. the reactants were flowed from the top inlet to the bottom outlet. Also, the inlets of the microreactor were connected to gas feed line and to a liquid feed line. The microreactor was properly cooled or heated as disclosed in detail in the following examples using a heat transfer fluid. In addition, before entering the microreactor, both the gas and the liquid were properly cooled or heated using two heat exchangers. The exhaust coolant and the biphasic flow containing the products left the microreactor via two separate ports.

$^{19}$F-NMR and $^1$H-NMR analyses were carried out on a Varian Mercury 300 MHz spectrometer using tetramethylsilane (TMS) as internal standard. $^{19}$F-NMR analyses were performed on a Varian Mercury 300 MHz spectrometer using $CFCl_3$ as internal standard.

Example 1—Synthesis of $CF_3CF_2OCF_2CF_2OCF_2COO^-K^+$

Step a —Synthesis of $C_2H_5OC_2H_4OC_2H_4OC(O)F$
In a 250 ml stainless steel reactor equipped with a mechanical stirrer, 100 g diethylenglycol monoethyl ether ($CH_3CH_2OCH_2CH_2OCH_2CH_2OH$) were loaded and maintained at 0° C. by an external cooling bath. 4.0 Nl/h Carbonyl difluoride ($COF_2$), synthesized by reaction between 4.0 Nl/h of $F_2$ and 5.0 Nl/h CO in a tubular reactor at 150° C., diluted with 10 Nl/h He were fed in the reactor through an inlet tube. $COF_2$ conversion was checked by gas chromatography (GC) analysis. After 5 h, the feeding of $COF_2$ was stopped and the excess dissolved in the crude reaction product was vented away by inert gas. The crude product was analysed by $^{19}$F-NMR and $^1$H-NMR; the analyses showed complete conversion of the starting alcohol and a selectivity in the desired fluoroformate higher than 98%.

Steps b and c—Synthesis of $CF_3CF_2OCF_2CF_2OCF_2COO^-K^+$

Step b. In a 250 ml stainless steel reactor equipped with a mechanical stirrer, two inlet tubes (tube A for fluorine and tube B for the fluoroformate from Step 1) and a condenser kept at −40° C., 100 ml 1,2,3,4-tetrachloro hexafluorobutane were loaded and maintained at 40° C. by an external heating bath; then elemental fluorine (5.0 Nl/h) diluted with He (15.0 Nl/h) was fed into the reactor by inlet tube A. After 30 minutes, 3.1 g/h of the fluoroformate from Step 1 (equivalent to 2.8 g/h pure fluoroformate) were fed in the reactor through inlet tube B. After 6 hours the feeding of the fluoroformate was interrupted and the reactor was cooled to 0° C. When this temperature was reached, 0.3 Nl/h $CF_3CF=CF_2$, diluted with 1.5 Nl/h He, were fed into the reactor through inlet tube B for 30 minutes, to convert all residual hydrogen atoms.

Step c. The resulting crude mixture was discharged in 400 g of 10% aqueous KOH to convert the perfluoroformate in the desired carboxylate and to neutralize all residual acidity. The two resulting phases were separated and the aqueous one was quantitatively analysed via $^{19}$F-NMR with an internal standard. $CF_3CF_2OCF_2CF_2OCF_2COO^-K^+$ was obtained with a 71% yield.

Example 2 (Comparative Example)—Synthesis of $CF_3CF_2OCF_2CF_2OCF_2COO^-K^+$ at Low Temperature Example 1 was repeated, with the difference that in Step b) the temperature was kept at −20° C. for the whole reaction time. Quantitative $^{19}$F-NMR analysis of the aqueous phase showed a $CF_3CF_2OCF_2CF_2OCF_2COO^-K^+$ yield of 28%.

Example 3—Synthesis of $CF_3CF_2OCF_2CF_2OCF_2COO^-K^+$ in a Falling Film Microreactor (FFMR) in the Presence of a Solvent The formate of formula $C_2H_5OC_2H_4OC_2H_4OC(O)F$ was synthesised according to Example 1, Step a).

Step b) was carried out in a FFMR, according to the following procedure. Fluorine (5.0 Nl/h), diluted with He (15.0 Nl/h) in a 1:3 volume ratio was fed into the reactor by an inlet tube (tube A), while 3.1 g/h of the formate from Example 1, Step a), mixed with 100 g/h 1,2,3,4-tetrachloro hexafluorobutane were fed in the reactor through an inlet tube B. The reactor was kept at a temperature of 40° C. by means of an external heating bath. The reaction product was condensed in a condenser cooled at −40° C. and the resulting liquid product was collected in a 500 ml stainless steel reactor equipped with a mechanical stirrer. After 6 hours the feeding of fluoroformate was interrupted, and the stainless steel reactor was cooled to 0° C. After this temperature was reached, 0.3 Nl/h $CF_3CF=CF_2$ diluted with 1.5 Nl/h He were fed into the reactor by an inlet tube C and 5 Nl/h $F_2$ diluted with He were fed by inlet tube D for 30 minutes to convert all residual hydrogen atoms. The resulting crude product was discharged in 400 g of 10% aqueous KOH to convert the perfluoroformate in the desired carboxylate and to neutralize all residual acidity. The two resulting phases were separated and the aqueous one was quantitatively analyzed via $^{19}$F-NMR with an internal standard. $CF_3CF_2OCF_2CF_2OCF_2COO^-K^+$ was obtained with a 80% yield.

Example 4—Synthesis of $CF_3CF_2OCF_2CF_2OCF_2COO^-K^+$ in a Falling Film Microreactor (FFMR) in the Absence of Solvent Example 3 was repeated, with the difference that fluorine (5.0 Nl/h), diluted with He (15.0 Nl/h) in a 1:3 volume ratio, was fed in the microreactor through inlet tube A, while 3.1 g/h of the fluoroformate from Example 1, Step a) was fed in the reactor through an inlet tube B. At the end of the reaction, the resulting mixture was worked-up in the same way as in Example 3, then 0.3 Nl/h $CF_3CF=CF_2$, diluted with 1.5 Nl/h He were fed in the reactor through an inlet tube C and 5 Nl/h F2 diluted with 5.0 Nl/h was fed through an inlet tube D for 30 minutes until complete fluorination. After treatment with 10% aqueous KOH, $CF_3CF_2OCF_2CF_2OCF_2COO^-K^+$ was obtained with a 75% yield.

The invention claimed is:
1. A method for manufacturing a fluorinated compound, the method comprising:
fluorinating a fluoroformate (I) with elemental fluorine, optionally in the presence of a (per)haloolefin, at a temperature of at least 20° C., to obtain the corresponding perfluorinated fluoroformate (III) and, optionally, cleaving the perfluorinated fluoroformate (III);
wherein fluoroformate (I) is the fluoroformate of an alcohol (II) comprising at least one —$CH_2OCH_2$— moiety.
2. The method according to claim 1 wherein alcohol (II) complies with formula (II-A):

$$R^1CH_2OH \qquad \text{(II-A)}$$

wherein $R^1$ is an optionally fluorinated straight or branched alkyl group comprising at least one ethereal oxygen atom comprised in a —$CH_2OCH_2$— moiety and, optionally, one or more further ethereal oxygen atoms and/or cycloalkylene moieties.

3. The method according to claim 2 wherein alcohol (II) complies with formula (II-B):

$$R^2-CH_2OCH_2(CH_2)_nOH \qquad (II-B)$$

wherein:
R² is an optionally fluorinated straight or branched alkyl group, optionally comprising at least one ethereal oxygen atom and/or cycloalkylene moiety and
n is an integer ranging from 1 to 10.

4. The method according to claim 3 wherein n ranges from 1 to 4.

5. The method according to claim 4 wherein alcohol (II) is selected from the group consisting of:
CH₃OCH₂CH₂OH
CH₃CH₂OCH₂CH₂OH
CH₃CH₂CH₂OCH₂CH₂OH
CH₃CH₂CH₂CH₂CH₂CH₂OCH₂CH₂OH
CH₃OCH₂CH₂OCH₂CH₂OH
CH₃CH₂OCH₂CH₂OCH₂CH₂OH
CH₃CH₂CH₂OCH₂CH₂OCH₂CH₂OH
CH₃CH₂CH₂CH₂OCH₂CH₂OCH₂CH₂OH
CH₃OCH₂CH₂CH₂OCH₂CH₂OH
CH₃OCH₂CH₂OCH₂CH₂OCH₂CH₂OH
CH₃CH₂OCH₂CH₂OCH₂CH₂OCH₂CH₂OH
CH₃CH₂CH₂OCH₂CH₂OCH₂CH₂OCH₂CH₂OH and
CH₃CH₂CH₂CH₂OCH₂CH₂OCH₂CH₂OCH₂CH₂OH.

6. The method according to claim 1, wherein the temperature ranges from 20° C. to 100° C.

7. The method according to claim 6 wherein the temperature ranges from 20° C. to 50° C.

8. The method according to claim 1, wherein cleaving the perfluorinated fluoroformate (III) is carried out by thermolysis in the presence of metal fluorides.

9. The method according to claim 1, wherein cleaving the perfluorinated fluoroformate (III) is carried out by treatment with a hydroxide.

10. The method according to claim 9 wherein the hydroxide complies with formula (f-1):

$$M^+OH^- \qquad (f\text{-}1)$$

wherein M represents a metal of group (I) of the periodic table or an ammonium group of formula $NR^N{}_4$, wherein $R^N$, equal to or different at each occurrence, is hydrogen or a $C_1$-$C_6$ hydrocarbon group.

11. The method according to claim 1, wherein fluorinating the fluoroformate (I) is carried out in a microreactor.

12. The method according to claim 6, wherein cleaving the perfluorinated fluoroformate (III) is carried out by thermolysis in the presence of metal fluorides.

13. The method according to claim 6, wherein cleaving the perfluorinated fluoroformate (III) is carried out by treatment with a hydroxide.

14. The method according to claim 6, wherein fluorinating the fluoroformate (I) is carried out in a microreactor.

15. The method according to claim 3, wherein the temperature ranges from 20° C. to 100° C.

16. The method according to claim 15, wherein the temperature ranges from 20° C. to 50° C.

17. The method according to claim 3, wherein cleaving the perfluorinated fluoroformate (III) is carried out by thermolysis in the presence of metal fluorides.

18. The method according to claim 3, wherein cleaving the perfluorinated fluoroformate (III) is carried out by treatment with a hydroxide.

19. The method according to claim 18 wherein the hydroxide complies with formula (f-1):

$$M^+OH^- \qquad (f\text{-}1)$$

wherein M represents a metal of group (I) of the periodic table or an ammonium group of formula $NR^N{}_4$, wherein $R^N$, equal to or different at each occurrence, is hydrogen or a $C_1$-$C_6$ hydrocarbon group.

20. The method according to claim 3, wherein fluorinating the fluoroformate (I) is carried out in a microreactor.

* * * * *